United States Patent
Palència-Adrubau et al.

(10) Patent No.: US 8,418,399 B2
(45) Date of Patent: Apr. 16, 2013

(54) TRAPPING DEVICE FOR FRUGIVOROUS INSECTS

(75) Inventors: Jaume Palència-Adrubau, Badalona (ES); Jaume Castellà-Solà, Badalona (ES); Mireia Barrot-Feixat, Barcelona (ES); Lídia Roura-Santos, Sabadell (ES)

(73) Assignee: Sociedad Española de Desarrollos Quimicos S.L., Barcelona (ES)

( * ) Notice: Subject to any disclaimer, the term of this patent is extended or adjusted under 35 U.S.C. 154(b) by 523 days.

(21) Appl. No.: 12/096,822

(22) PCT Filed: Nov. 20, 2006

(86) PCT No.: PCT/EP2006/011135
§ 371 (c)(1),
(2), (4) Date: Jun. 10, 2008

(87) PCT Pub. No.: WO2007/068329
PCT Pub. Date: Jun. 21, 2007

(65) Prior Publication Data
US 2009/0000180 A1    Jan. 1, 2009

(30) Foreign Application Priority Data
Dec. 16, 2005    (ES) .................................. 200503100

(51) Int. Cl.
*A01M 1/02*    (2006.01)
*A01M 1/10*    (2006.01)

(52) U.S. Cl.
USPC .............................................. 43/107; 43/122

(58) Field of Classification Search .................... 43/107, 43/122
See application file for complete search history.

(56) References Cited

U.S. PATENT DOCUMENTS

| | | | | |
|---|---|---|---|---|
| 2,979,856 A | * | 4/1961 | Ponting ........................ | 43/132.1 |
| 3,030,267 A | * | 4/1962 | Margot ............................ | 43/124 |
| 3,294,816 A | * | 12/1966 | Latos et al. .................... | 548/419 |
| 3,940,488 A | * | 2/1976 | Frohberger et al. ........... | 514/478 |
| 3,989,815 A | * | 11/1976 | Rajadhyaksha ................. | 424/60 |

(Continued)

FOREIGN PATENT DOCUMENTS

| AT | 385 628 B | | 4/1988 |
|---|---|---|---|
| CH | 672874 AS | * | 1/1990 |

(Continued)

OTHER PUBLICATIONS

"Success Controlling Medfly", Science Daily, Science News, Jul. 26, 2005 [retrieved on Mar. 26, 2010]. Retrieved from the Internet<URL: http://www.sciencedaily.com/releases/2005/07/050726125755.htm.*

(Continued)

*Primary Examiner* — Darren W Ark
(74) *Attorney, Agent, or Firm* — McGlew and Tuttle, P.C.

(57) ABSTRACT

Trapping device for frugivorous insects. The device comprises trapping means and a single diffuser of attractant means arranged inside the trapping means. The diffuser is made up of a container containing inside a support material. This support material, which is of the porous type, is impregnated with a solution comprising a diaminoalkane, ammonium acetate and trimethylamine.

19 Claims, 5 Drawing Sheets

U.S. PATENT DOCUMENTS

| | | | |
|---|---|---|---|
| 4,283,878 A * | 8/1981 | Hill et al. | 43/122 |
| 4,310,985 A * | 1/1982 | Foster et al. | 43/131 |
| 4,400,903 A * | 8/1983 | Seidenberger | 43/122 |
| 4,525,199 A * | 6/1985 | Rajakhyaksha | 504/358 |
| 4,551,941 A * | 11/1985 | Schneidmiller | 43/122 |
| 4,571,880 A * | 2/1986 | Hayward | 43/122 |
| 4,662,103 A * | 5/1987 | Cheng | 43/132.1 |
| 4,694,604 A * | 9/1987 | Mitchell | 43/122 |
| 4,813,174 A * | 3/1989 | Cook | 43/107 |
| 4,899,485 A * | 2/1990 | Schneidmiller | 43/122 |
| 4,908,977 A * | 3/1990 | Foster | 43/122 |
| 5,046,280 A * | 9/1991 | Foster et al. | 43/107 |
| 5,150,541 A * | 9/1992 | Foster et al. | 43/131 |
| 5,452,540 A * | 9/1995 | Dowd et al. | 43/107 |
| 5,750,129 A * | 5/1998 | Wakarchuk | 424/84 |
| 5,766,617 A * | 6/1998 | Heath et al. | 424/410 |
| 5,839,221 A * | 11/1998 | Ron et al. | 43/132.1 |
| 5,907,923 A * | 6/1999 | Heath et al. | 43/122 |
| 5,939,062 A * | 8/1999 | Heath et al. | 424/84 |
| 5,992,087 A * | 11/1999 | Chu et al. | 43/122 |
| 6,018,905 A * | 2/2000 | Lingren | 43/107 |
| 6,019,964 A * | 2/2000 | Liquido et al. | 424/84 |
| 6,112,454 A * | 9/2000 | Plato et al. | 43/122 |
| 6,138,402 A * | 10/2000 | Wotton | 43/122 |
| 6,190,653 B1 * | 2/2001 | Landolt et al. | 43/132.1 |
| 6,224,890 B1 * | 5/2001 | Heath et al. | 43/107 |
| 6,264,939 B1 * | 7/2001 | Light et al. | 43/107 |
| 6,344,191 B2 * | 2/2002 | Landolt et al. | 43/107 |
| 6,393,760 B1 * | 5/2002 | Lingren | 43/122 |
| 6,516,558 B1 * | 2/2003 | Lingren et al. | 43/107 |
| 6,528,049 B2 * | 3/2003 | Light et al. | 43/107 |
| 6,532,695 B1 * | 3/2003 | Alvarado | 43/122 |
| 6,543,181 B1 * | 4/2003 | Baker et al. | 43/107 |
| 6,546,668 B1 * | 4/2003 | Ball et al. | 43/122 |
| 6,625,922 B1 * | 9/2003 | Ernsberger, IV | 43/122 |
| 6,708,445 B1 * | 3/2004 | Israely | 43/132.1 |
| 6,821,526 B1 * | 11/2004 | Huang | 43/122 |
| 6,966,142 B1 * | 11/2005 | Hogsette et al. | 43/122 |
| 7,082,712 B2 * | 8/2006 | Harris et al. | 43/122 |
| 7,290,368 B2 * | 11/2007 | Rich et al. | 43/122 |
| 7,310,907 B2 * | 12/2007 | Suteerawanit | 43/122 |
| 7,712,248 B2 * | 5/2010 | Beroza | 43/122 |
| 7,856,753 B2 * | 12/2010 | Fisher | 43/122 |
| 7,913,449 B2 * | 3/2011 | Beroza | 43/122 |
| 2002/0144452 A1 * | 10/2002 | Beroza | 43/107 |
| 2003/0049296 A1 * | 3/2003 | Knauf et al. | 43/107 |
| 2004/0185080 A1 * | 9/2004 | Hojo et al. | 43/107 |
| 2004/0216369 A1 * | 11/2004 | Beroza | 43/131 |
| 2005/0144831 A1 * | 7/2005 | Knauf et al. | 43/107 |
| 2007/0094915 A1 * | 5/2007 | Plato et al. | 43/107 |
| 2007/0148202 A1 * | 6/2007 | Primo Yufera et al. | 424/410 |
| 2008/0086932 A1 * | 4/2008 | Cook et al. | 43/107 |
| 2008/0196296 A1 * | 8/2008 | Studer et al. | 43/122 |
| 2009/0084024 A1 * | 4/2009 | Hamilton Baxter | 43/107 |
| 2009/0126257 A1 * | 5/2009 | Banfield | 43/122 |
| 2009/0151228 A1 * | 6/2009 | Schneidmiller | 43/122 |
| 2009/0293342 A1 * | 12/2009 | Winkler | 43/107 |
| 2010/0154289 A1 * | 6/2010 | Fisher | 43/107 |
| 2010/0154290 A1 * | 6/2010 | Fisher | 43/107 |

FOREIGN PATENT DOCUMENTS

| | | |
|---|---|---|
| ES | U9901125 | 11/1999 |
| JP | 08-269035 | 10/1996 |
| WO | WO 9529585 A2 * | 11/1995 |

OTHER PUBLICATIONS http://www.extento.hawaii.edu/fruitfly/images/poster/biolure.pdf, "Hawaii Area—Wide Fruit Fly Pest Management Brochure", Jul. 13, 2004.

http://www.extento.hawaii.edu/fruitfly/images/to%20post/biolure.pdf, "Hawaii Area—wide Fruit Fly Integrated Pest Management Program Brochure", Jul. 12, 2004.

Jang et al., Evaluation of a Single-Matrix Food Attractant Tephritid Fruit Fly Bait Dispenser for Use in Federal Trap Detection Programs, Proc. Hawaiian Entomological Society (2007) 39:1-8, see https://scholarspace.manoa.hawaii.edu/handle/10125/839.

* cited by examiner

TRAPPING DEVICE FOR FRUGIVOROUS INSECTS

FIELD OF THE INVENTION

The invention relates to a trapping device for frugivorous insects.

STATE OF THE ART

Frugivorous insects and frugivorous flies in particular, cause serious economic losses in the production of fruit and vegetables. Therefore, in this sector, controlling plagues of this type of flies has gained importance in recent years.

In the state of the art, for some time attractants and insecticides have been applied which, for example, are applied through fumigation, using an airplane. However, the growing concern for protecting the environment has led to the introduction of more selective and less pollutant methods, such as for example, the trapping technique. This technique consists in attracting and killing adult insects inside a trap. The insects are attracted towards the trap by attractant substance vapour diffusers, and then they are killed with an insecticide vapour diffuser. This technique can be used to trace the insect's flight path, in other words, to detect the presence of the insect using a small number of traps per cultivation surface area unit, and then to decide the most suitable moment to apply the control treatments using conventional insecticides. Moreover, this technique can also be used directly to control plagues, using a large scale trap, in other words, with a greater number of traps per cultivation surface area unit, which is intended to capture and kill the maximum number of adult insects.

An example of the application of this technique can be seen with the fruit fly, *Ceratitis capitata* Wied (Diptera, Tephritidae), which causes serious problems in the cultivation of citrus and bone or pip fruits. To combat the effects this fly produces, it is known to use attractants that are more effective and selective in attracting female insects, which are the essential target for controlling the damage produced by the plague. Said attractants are ammonium acetate, 1,4-diaminobutane (putrescine) or 1,5-diaminopentane (cadaverine) and trimethylamine. The ammonium acetate and the two diaminoalkanes are used as food, and the trimethylamine is used to strengthen the attraction capacity of the two previous components. In order to attract the adult insects effectively, three individual diffusers are used, one for the ammonium acetate in aqueous solution, a second one for the 1,4-diaminobutane or the 1,5-diaminopentane in the pure liquid state, and a third one for the trimethylamine, also in aqueous solution. The attractants combine with an insecticide placed inside an additional diffuser that is used to kill the insects. Various active substances can be used as insecticides. The most commonly used is 2,2-dichlorovinyl dimethyl phosphate, also known as DDVP or DICHLORVOS.

One of the drawbacks of this technique lies in the fact that the system's effectiveness is not guaranteed throughout the ripening and harvesting period of the fruit in question, since the diffusers have to be replaced approximately half way through the production campaign, if the large scale trap is to be really effective. Therefore, having to replace three diffusers per trap, with the subsequent material costs and the cost of the work force entrusted with replacing said diffusers, means that this system is not economical, and therefore, not very competitive.

An additional drawback associated with this technique is that in the diffusers that do not use a membrane, owing to the high hygroscopicity of the ammonium acetate diffuser, the traps end up with liquid phases, which make it difficult to count and control the number of trapped insects. In the diffusers that do use a membrane, the most commonly used nowadays is a permeable membrane, which lets water and solutions in the liquid phase pass in and out of the diffusers. In certain cases, this leads to the formation of attractant crystals on the membrane's external surface, and this alters the emission of the attractants and leads to a reduced number of insects captured in the trap. Moreover, it also reduces the trap's service life. These factors also affect the final cost of the trap, and also possibly the cost of the harvest that is ruined by the system's inefficiency.

DISCLOSURE OF THE INVENTION

The aim of the invention is to overcome said drawbacks. This aim is achieved by means of a trapping device of the type indicated at the beginning, characterised in that it comprises
   trapping means and a single diffuser of attractant means arranged inside said trapping means,
   where said diffuser comprises a container, with said container containing a support material inside,
   and in that said support material is impregnated with a solution comprising diaminoalkane, ammonium acetate and trimethylamine.

Preferably, the container comprises at least one opening, said opening being covered by membrane means. Moreover, preferably, the solution is an aqueous solution. This is a noticeable advantage over the state of the art insofar as the economic cost of the trapping device is concerned. Not only is the number of diffusers in each trapping means reduced, but also the replacement costs of worn diffusers is also reduced, as in this case only one diffuser is needed.

However, one of the main drawbacks to overcome during the development was to succeed in effectively combining the attractants in one single diffuser. To this end, it was necessary to obtain a solution wherein the diaminoalkane could behave correctly in the form of an aqueous solution and in particular, in conditions that prevented the permeation of liquid phases which, as explained in detail above, it was noticed, during the development of the invention, that it led to crystals of the attractant product forming on the diffuser's surface. This effect reduced the diffuser's effectiveness, and therefore its attractant effect, and also shortened its service life.

This problem meant that the membrane had to be optimised so as to let vapour through but not water. This factor proved decisive and introduced important advantages. First of all, the humidity inside the diffuser was maintained, thus prolonging its effectiveness. Also, the formation of attractant crystals on the membrane was avoided, because the diffuser did not allow any aqueous liquid phases to permeate. Therefore, although the trap contains a humid diffuser inside, the trap itself is actually dry. To achieve this effect, the membrane diffusion means are made up of at least one sheet of non-woven type plastics, such as for example, the one made by the company DUPONT under the commercial name TYVEK®. The diffuser preferably improves its properties if the container is made from an impermeable material consisting of a sheet comprising an aluminium/polyethylene/polyester complex, and if the support material is porous, such as for example, cellulose. Therefore, the only vapour inlet and outlet is through the membrane, which in turn prevents liquid aqueous phases from entering and leaving the diffuser. Moreover, it is worth mentioning that the membrane material is also suitable for emitting other attractants, including, inter alia, for example, insect pheromones.

Other commonly used support materials exist, which comprise polysulfones, nylons, polycarbonates, polyvinidylene chloride, cellulose and its esters, polyolefins, polyurethanes, polyvinylic alcohols, epoxy resins and polyvinyl chlorides, their pores allowing the attractant to be retained by virtue of capillary motion.

Also, as for regulating the emission speed, in general, this is done by varying the nature, thickness and/or surface of the semi-permeable membrane. The membrane materials can be as follows: non-woven polyethylene or polypropylene fabric or others.

At any event, in order to function optimally, according to the invention, the membrane means have a water vapour transfer rate (MVTR) that is preferably greater than 1500 $g/m^2/day$. Moreover, advantageously, the diaminoalkane is 1,5-diaminopentane.

During the development of this invention, another of the basic aims was to succeed in increasing the duration of the diffusers. Surprisingly, it was observed that the decisive factor in the duration of the trapping system's efficiency was the amount of ammonium acetate contained in the initial formula. Therefore, preferably, the ammonium-acetate/1,5-diaminopentane proportion of said solution is comprised between 100 and 1000 and preferably 160 and 850. So, already in the initial development phase, it was observed that in the case of the three separate diffusers, by appropriately increasing the amount of the substance in the ammonium acetate diffuser, without modifying the loads in the other diffusers, the trap's service life doubled, with the subsequent reduction in the costs of the trapping process because the replacement operation was no longer necessary.

Preferably, the membrane has one such characteristic whereby the diffusion speed of the ammonium acetate is greater than 60 mg/day and preferably greater than 70 mg/day. This characteristic has proved particularly effective. In particular, it was observed that at a greater diffusion speed, a greater number of insects were captured, particularly in the initial trapping phase.

Preferably, the invention also comprises an insecticide diffuser. Advantageously, the insecticide diffuser contains 2,2-dichlorovinyl dimethyl phosphate.

BRIEF DESCRIPTION OF THE DRAWINGS

Other advantages and characteristics of the invention are apparent from the following description, in which, some preferred, non-limiting, embodiments of the invention are described, with reference to the accompanying drawings, in which.

DETAILED DESCRIPTION OF AN
EMBODIMENT OF THE INVENTION

Figure 1:
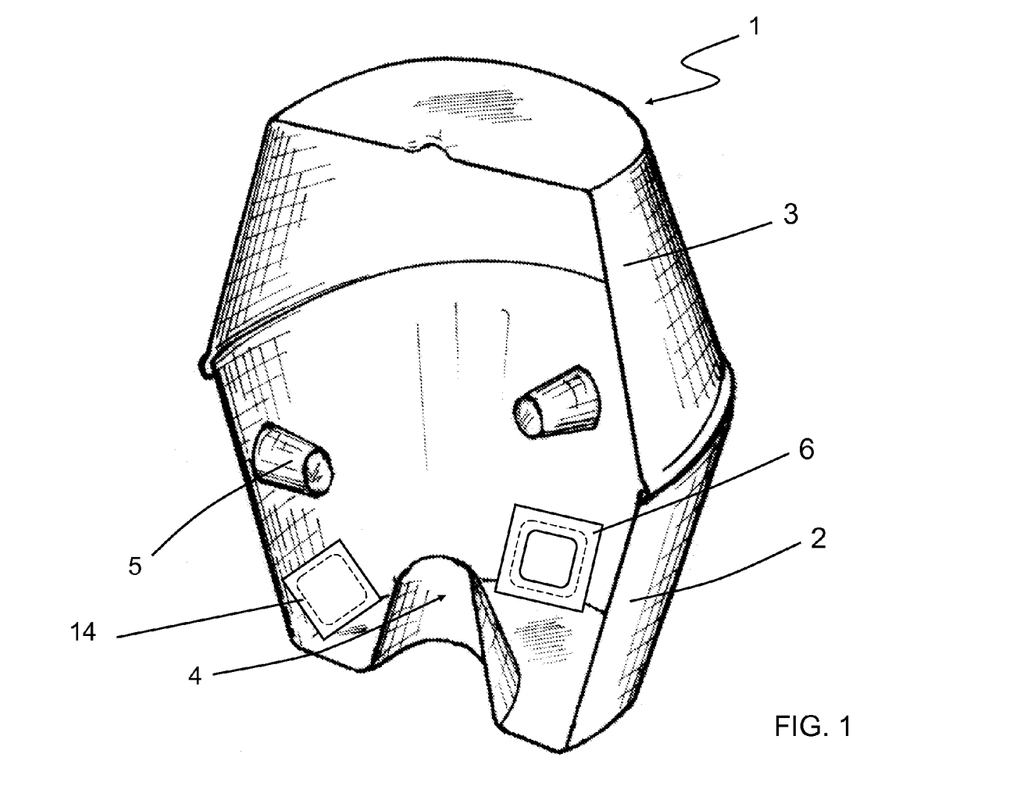
FIG. 1, a perspective view of trapping means sectioned along a central plane.

FIG. 1 represents a perspective view of the trapping means 1 sectioned along a central plane. Trapping means 1, or traps, consists normally of a lower, opaque bucket 2 of attractant colours for frugivorous insects and a transparent lid 3. In the bottom part of bucket 2 a frustoconical forming 4 is provided and on the sides, three radial channels 5, for example, are provided, but not exclusively, at 120°, which, as well as facilitating the diffusion of the attractants outwards, prevent the insects that have entered trap 1 from leaving. A more detailed explanation of these characteristics is provided in Spanish Utility Model No. ES-U9901125.

Figure 2:
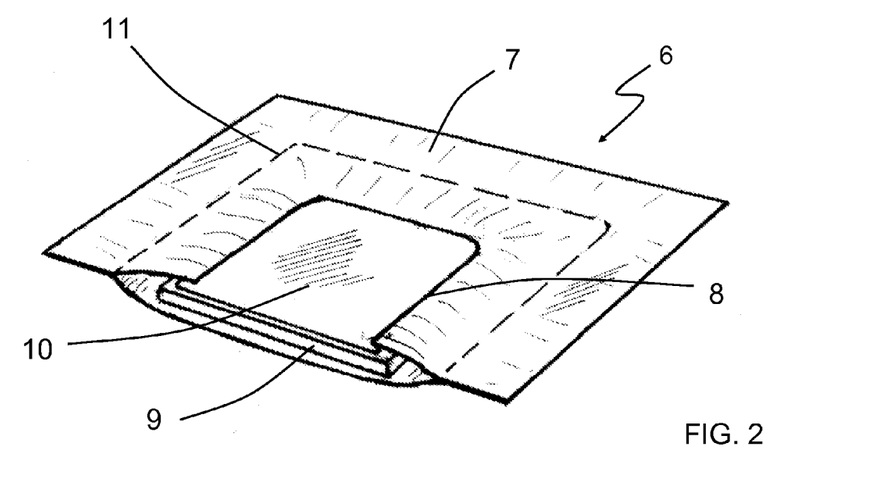
FIG. 2, a perspective view of a finished diffuser for attractant means sectioned at along its middle plane.

FIG. 2 shows as an example, a possible structure of a diffuser 6 finished according to the invention. Said diffuser comprises a container 7 of permeable material, such as a sheet made from an aluminium/polyethylene/polyester complex, or any other material that is impermeable to the chemical substance that has to be contained. Said container has an opening 8, in this case rectangular, although other shapes are feasible. Both for container 7 and opening 8 other shapes are conceivable such as for example circular, square, elliptical, or others. Opening 8 closes towards the outside thanks to a membrane 10 made from non-woven fabric type plastics, such as for example the material made by the company DUPONT under the commercial name of TYVEK®, which allow vapours to be emitted in a controlled manner. It was precisely the application of a membrane having these characteristics that was the key to discovering the solution of using one single diffuser. Inside container 7 a cellulose support material 9 is arranged that is impregnated with the attractant substance and/or attractant effect strengthening agent. In the initial situation, container 7 is shaped like a bag with two welding lines 11. Once filled with support material 9 and soaked in the attractant solution, the container is sealed definitively on its open side, for example by thermowelding, in order to close it definitively.

Figure 3:
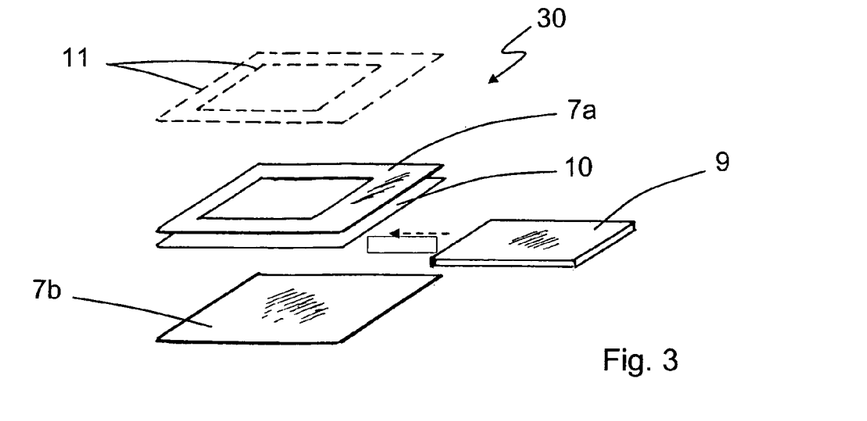
FIG. 3, an exploded perspective view of the structure of an ammonium acetate diffuser according to the invention.
Figure 4:
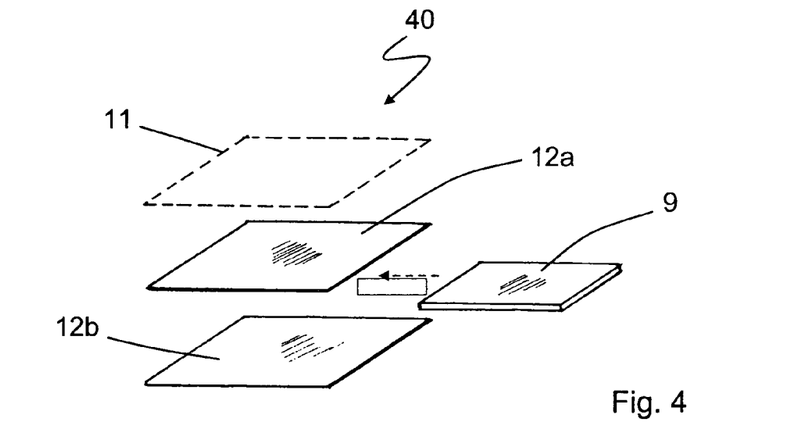
FIG. 4, an exploded perspective view of the structure of a trimethylamine diffuser according to the invention.
Figure 5:
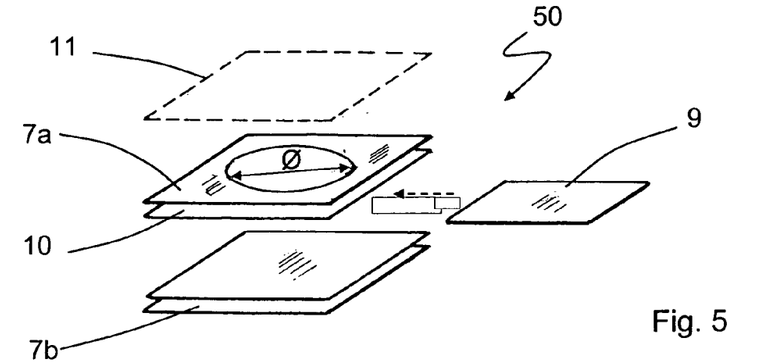
FIG. 5, an exploded perspective view of the structure of a diaminoalkane diffuser according to the invention.

FIGS. 3 through 5 show practical embodiment examples of diffusers 30, 40, 50 for the various attractants according to the invention.

FIG. 3 shows a diffuser 30 for ammonium acetate having a general structure similar to that of diffuser 6 in FIG. 2, wherein the characteristic dimensions for container 7a, 7b are: 88×80 mm; for support 9 are: 55×68×2 mm and for the rectangular opening 8 in container 7 are: 42×40 mm.

FIG. 4 shows a diffuser 40 for trimethylamine which, contrary to diffuser 6 in FIG. 2, is only made up of one container 12a, 12b made from sheets of different non-woven fabric type plastics, and in particular, sheets of non-woven polyethylene fabric (TYVEK®) measuring 88×80 mm, which inside contains a cellulose support material 9 with dimensions 60×55×2 mm.

Finally, FIG. 5 shows a diffuser 50 for diaminoalkane with similar characteristics to the one shown in FIG. 3, but in which the opening is circular, having a Ø=34 mm and the membrane is made from mono-orientated polyethylene.

Trapping means 1 shown in FIG. 1 and diffusers 30, 40, 50 shown in FIGS. 3 through 5 were used for the practical development of the invention.

Generally, tracing the flight or controlling the plague of frugivorous insects is carried out between 30 and 40 days before the harvest, in other words before the fruit has ripened, and therefore before it changes its colour. Once traps 1 are assembled, in other words once diffusers 30, 40, 50 have been introduced into traps 1, said traps are hung from the fruit trees at a height between 1.4 and 1.8 m from the ground, envisaging, in the case of plague control, an initial density of, for example, 35 to 40 traps per hectare. In most cases, a detailed study on the insect's development conditions makes it possible to reduce the number of traps per hectare by applying movement techniques, perimetral techniques or by simply reducing the dose. In order to know the population level of the insect at all times, it is advisable to run a weekly check on traps 1 which can be considered representatives of the estate, so that the number of examples captured can be noted.

In particular, during the development of the invention, different large scale trap experiments were carried out. A detailed explanation is provided below on the main results obtained from the experiments.

Example 1

The aim of a first experiment was to ascertain that an increased load of ammonium acetate determined a greater duration of the insect capturing efficiency period for all three attractant diffusers, without the need to modify the load of the other two. Moreover, the experiment was also aimed at proving that the greater the diffusion, the greater the number of insects captured.

Diffusers were prepared in the following way for a large scale trapping:

A first diffuser 30, similar to the one in FIG. 3, (with the container consisting of a sheet made from an aluminium/polyethylene/polyester complex; non-woven polyethylene fabric membrane (TYVEK®) and cellulose support) was loaded with 4.25 g of ammonium acetate from an aqueous solution of ammonium acetate at 67% w/w (weight/weight) and 33% w/w water.

A second type of diffuser 30, similar to the one in FIG. 3, (with the container consisting of a sheet made from an aluminium/polyethylene/polyester complex; non-woven polyethylene fabric membrane (TYVEK®) and cellulose support) was loaded with 7.8 g of ammonium acetate from an aqueous solution of ammonium acetate at 67% w/w and 33% w/w water.

A third type of diffuser 40, like the one in FIG. 4, (with container-non-woven polyethylene membrane (TYVEK®) and cellulose support), was loaded with an aqueous solution of trimethylamine hydrochloride at 70% w/w and 30% w/w water. The amount equivalent to 0.78 g of trimethylamine hydrochloride was placed in each diffuser.

A fourth type of diffuser 50, like the one in FIG. 5, (with the container consisting of a sheet made from an aluminium/polyethylene/polyester complex; mono-oriented polyethylene membrane and cellulose support) was loaded with 0.035 ml of cadaverine in the liquid state at 100% w/w. The equivalent amount in weight was approximately 0.035 g of cadaverine.

Insecticide diffusers with 0.20 g of DDVP were also provided.

Finally traps were prepared with the following combinations of the above-mentioned diffusers.

A1, 3 diffusers:
Ammonium acetate diffuser with 7.8 g of the product.
Trimethylamine hydrochloride diffuser with 0.78 g of the product.
Cadaverine diffuser with 0.035 g of the product.
A3, 3 diffusers
Ammonium acetate diffuser with 4.25 g of the product.
Trimethylamine hydrochloride diffuser with 0.78 g of the product.
Cadaverine diffuser with 0.035 g of the product.

The test consisted in determining the number of adult insects captured by the attractants containing different amounts of ammonium acetate. The test was conducted simultaneously in various peach and citrus tree plantations. A total of 3 batteries (repetitions) of traps were placed in each plantation, one for each of the test variants. The traps were distanced approximately 30 m from each other to prevent any interference. The traps used were those disclosed in Spanish Utility Model No. U9901125. They were inspected 3 times a week. During each inspection, the number of adult *Ceratitis capitata* captured in each trap was noted, and a distinction was made between males and females. In order to avoid any influence related to the trap's location, on each inspection day, all the traps in each battery were rotated.

Figure 6:
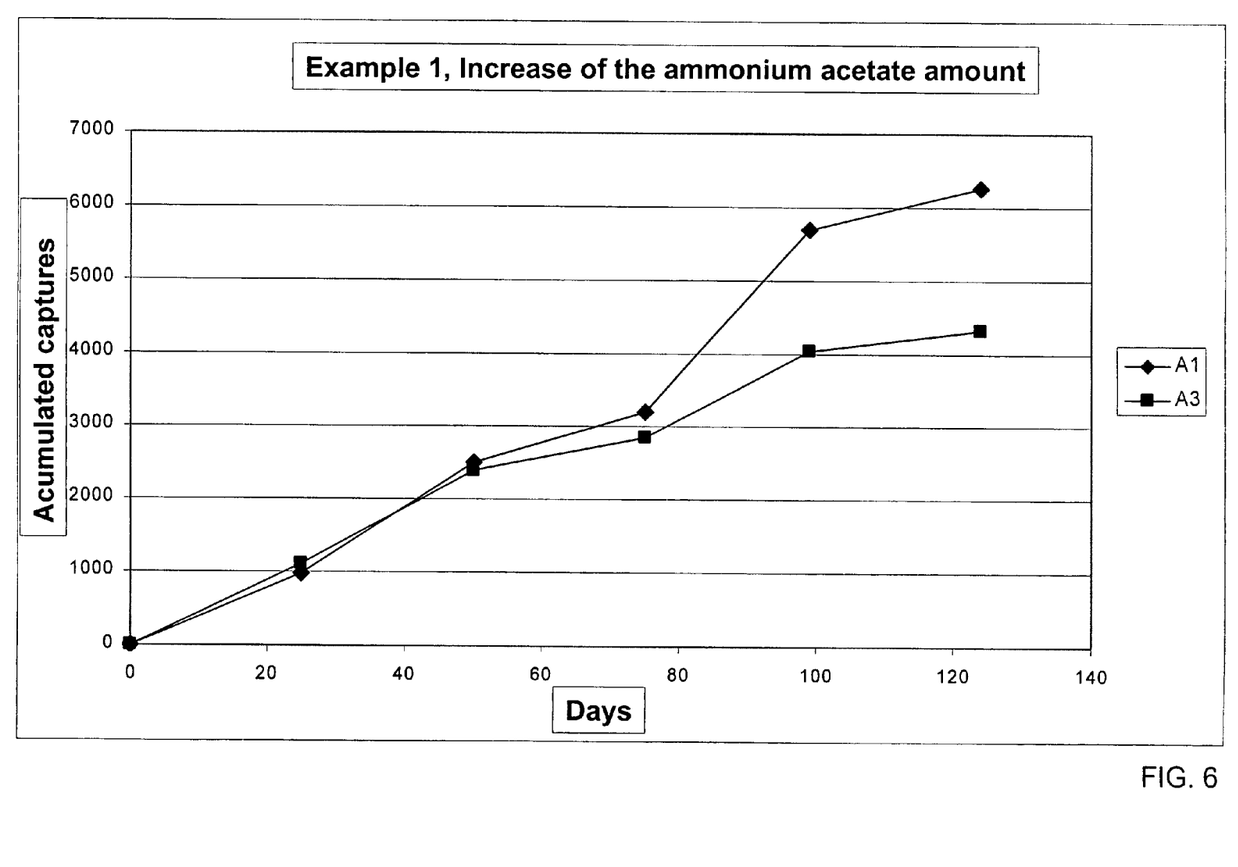
FIG. 6, a comparative diagram showing the greater duration of the trap's effectiveness by increasing the amount of ammonium acetate.

The test results are shown in FIG. 6.

The product containing a smaller amount of ammonium acetate began to reveal reduced efficiency after 50 days (reduced slope with respect to the product containing the largest amount). This reduction progressed over time. Therefore the total number of insects captured during the 120-day test period was 48% higher with the diffuser containing the largest amount of ammonium acetate, and 205% higher when considering the period from 50 to 120 days.

Example 2

A second experiment revealed that when the 1,5 diaminopentane, ammonium acetate and trimethylamine are contained in one single diffuser of the type and materials mentioned in the description, the system's efficiency is virtually equal to using a separate diffuser for each chemical component.

The field test protocol is the same as that used in Example 1.

According to the description, diffusers were prepared as follows for a large scale trap:

A first type of diffuser 30, similar to the one in FIG. 3, (with the container consisting of a sheet made from an aluminium/polyethylene/polyester complex; non-woven polyethylene fabric membrane (TYVEK®) and cellulose support) was loaded with 7.8 g of ammonium acetate from an aqueous solution of ammonium acetate at 67% w/w and 33% w/w water.

A second type of diffuser 40, like the one in FIG. 4, (with non-woven polyethylene container-membrane (TYVEK®) and cellulose support), was loaded with an aqueous solution of trimethylamine hydrochloride at 70% w/w and at 30% w/w water. The amount equivalent to 0.78 g of trimethylamine hydrochloride was placed in each diffuser.

A third type of diffuser 50, like the one in FIG. 5, (with the container consisting of a sheet made from an aluminium/polyethylene/polyester complex; mono orientated polyethylene membrane and cellulose support) was loaded with 0.03 ml of cadaverine in the liquid state at 100% w/w. The equivalent amount in weight was approximately 0.035 g of cadaverine.

A fourth diffuser 30 was also prepared, similar to the type in FIG. 3, with a container consisting of a sheet made from an aluminium/polyethylene/polyester complex; non-woven polyethylene fabric membrane (TYVEK®) and cellulose support containing an aqueous solution made up of the above-mentioned components, in particular 61% w/w ammonium acetate, 6.1% w/w trimethylamine hydrochloride, 0.28% w/w cadaverine and 32.62% w/w water. The equivalent amounts of attractants were 7.8 g of ammonium acetate, 0.78 g of trimethylamine hydrochloride and 0.035 g of cadaverine. The diffuser was filled with 11.5 ml of each solution.

Insecticide diffusers 14 with 0.20 g of DDVP were also provided.

Finally the traps were prepared with the following formulae:

A1, 3 diffusers:
Ammonium acetate in diffuser according to FIG. 3, with 7.8 g of the product.
Trimethylamine hydrochloride in diffuser according to FIG. 4, with 0.78 g of the product.
Cadaverine in diffuser according to FIG. 5, with 35 mg of the product.

A2, 1 diffuser:
According to FIG. 3, with 7.8 g of ammonium acetate, 0.78 g of trimethylamine hydrochloride and 35 mg of cadaverine.

Figure 7:
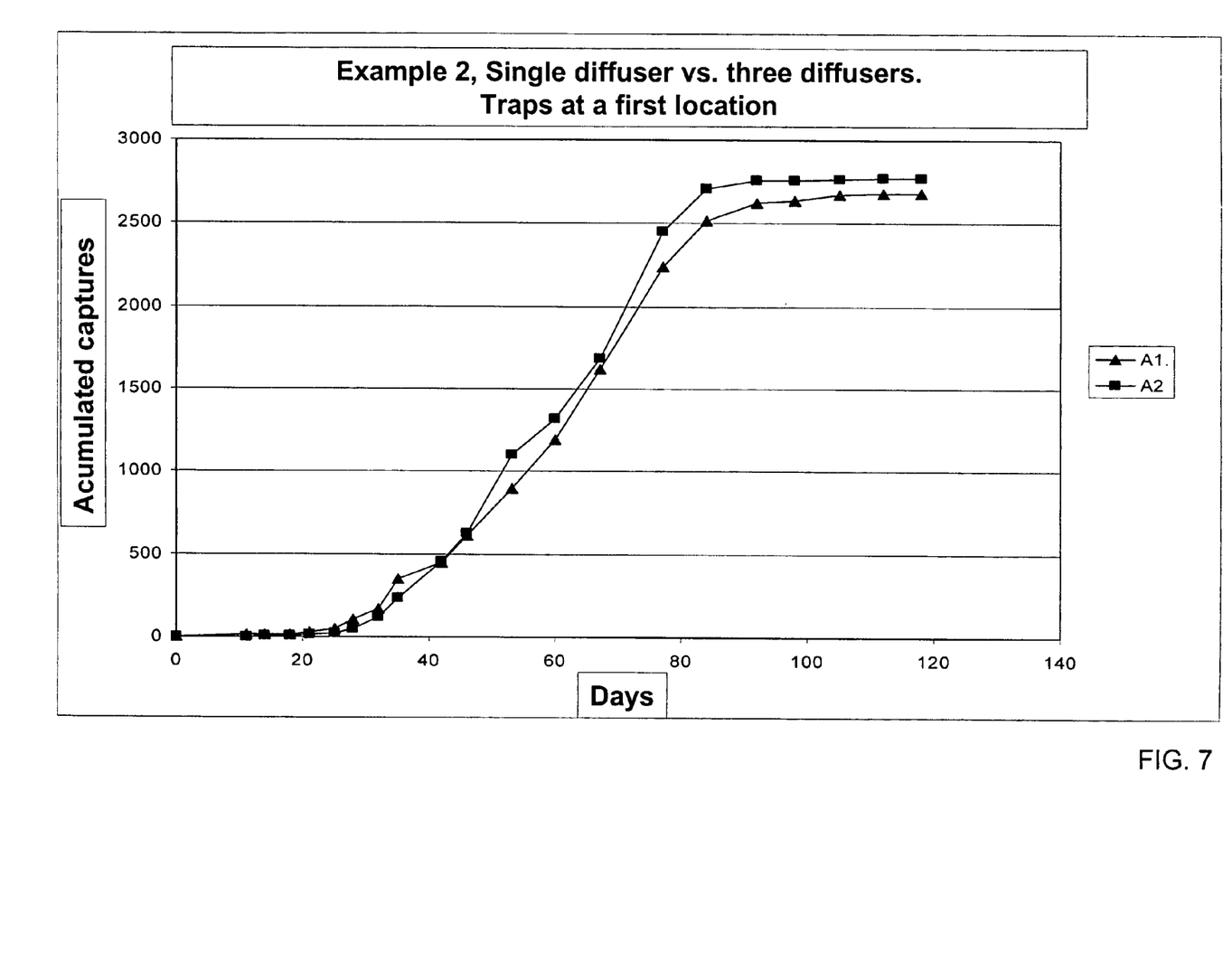
FIG. 7, a comparative diagram showing the efficiency of a single attractant substance diffuser versus the using of three diffusers, at a first location.
Figure 8:
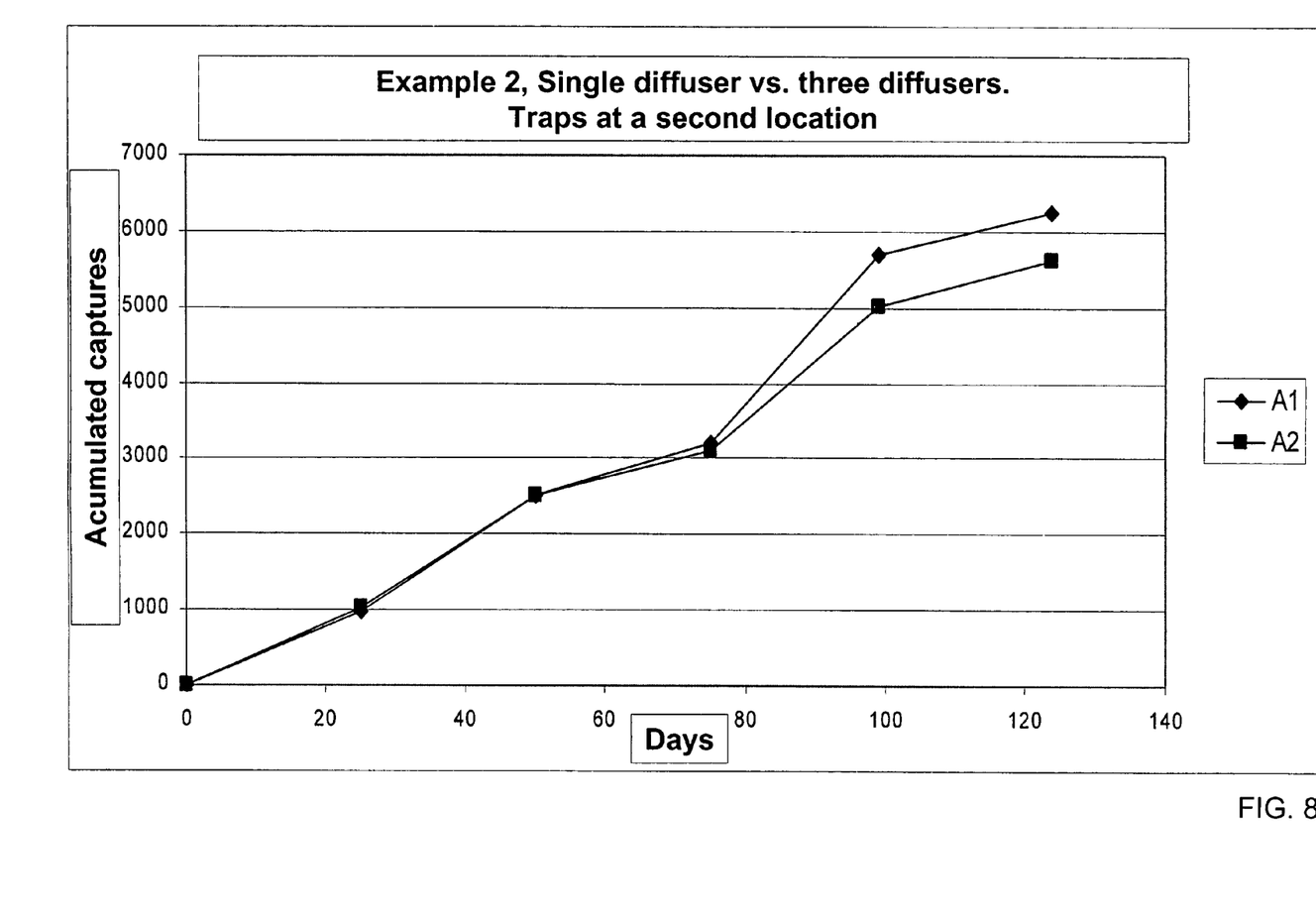
FIG. 8, a comparative diagram showing the efficiency of a single attractant substance diffuser versus the using of three diffusers, at a second location

FIGS. 7 and 8 show the results obtained when comparing the use of one diffuser for each product, with the use of one single diffuser for the simultaneous emission of all three products, with each of the tests being carried out at a different location.

Therefore, as shown in FIGS. 7 and 8, incorporating the three compounds in one single diffuser, prepared as explained in the description, does not jeopardise the trapping method's efficiency.

Therefore it has been proved that an increased amount of ammonium acetate determines a greater capture efficiency period for all three attractant diffusers, without the need to modify the load in the other two. Moreover, the greater capture efficiency is evident when using one single diffuser for the three chemical substances.

In this way, as shown, the trapping device according to the invention represents a substantial improvement over the known state of the art methods. Also, by providing all the chemical components in one single diffuser and extending their efficiency period from 60 to 120 days, the costs of large scale traps for catching frugivorous insects can be reduced advantageously, on the one hand because the direct cost of the material used is cheaper, and also because the diffuser replacement costs are avoided.

The invention claimed is:

1. A trapping device for frugivorous insects, the device comprising:
a trapping means and a single diffuser of attractant means arranged inside said trapping means, said diffuser comprising a container, said container defining an interior, said container containing a support material within said interior, said support material being impregnated with a *Ceratitis Capitata* attractant solution comprising a diaminoalkane, ammonium acetate and trimethylamine, said diaminoalkane being 1,5-diaminopentane.

2. A trapping device according to claim 1, wherein said container comprises at least one opening, said at least one opening being covered by a membrane means for diffusion.

3. A trapping device according to claim 2, wherein said membrane means for diffusion includes at least one sheet of non-woven fabric type plastics.

4. A trapping device according to claim 3, wherein said container comprises an impermeable material which consists of a sheet comprising an aluminum/polyethylene/polyester complex and said support material is porous.

5. A trapping device according to claim 2, wherein said container comprises an impermeable material which consists of a sheet comprising an aluminum/polyethylene/polyester complex and said support material is porous.

6. A trapping device according to claim 5, wherein said support material comprises cellulose.

7. A trapping device according to claim 2, wherein said membrane means has a water vapor transfer rate (MVTR) greater than 1500 g/m$^2$/day.

8. A trapping device according to claim 2, wherein said membrane means is composed of a vapor permeable and liquid impermeable material.

9. A trapping device according to claim 1, wherein said solution is an aqueous solution.

10. A trapping device according to claim 1, wherein a weight proportion of ammonium acetate/1,5-diaminopentane in said solution is between 100 and 1000 and preferably between 160 and 850.

11. A trapping device according to claim 1, wherein a diffusion speed of said ammonium acetate is greater than 60 mg/day and preferably greater than 70 mg/day.

12. A trapping device according to claim 1, further comprising an insecticide diffuser.

13. A trapping device according to claim 12, wherein said insecticide diffuser contains 2,2-dichlorovinyl dimethyl phosphate.

14. A trapping device for frugivorous insects, the device comprising:
a trapping means for trapping insects; and
a single diffuser arranged in an interior space of said trapping means, said diffuser comprising a container, said container defining a container interior space, said container comprising a support material arranged within said container interior space, said support material comprising a *Ceratitis Capitata* attractant solution, said *Ceratitis Capitata* attractant solution consisting essentially of a 1,5-diaminopentane, ammonium acetate and trimethylamine, wherein vapor from said *Ceratitis Capitata* attractant solution diffuses into said trapping means via said single diffuser such that said vapor of said *Ceratitis Capitata* attractant solution attracts one or more insects into said interior space of said trapping means.

15. A trapping device in accordance with claim 14, wherein said container comprises at least one opening and a membrane, said at least one opening being covered by said membrane, wherein said vapor of said attractant solution passes through said membrane.

16. A trapping device in accordance with claim 15, wherein said membrane includes at least one sheet of non-woven fabric type plastics.

17. A trapping device in accordance with claim 15, wherein said container comprises an impermeable material which consists of a sheet comprising an aluminum/polyethylene/polyester complex and said support material is porous.

18. A trapping device in accordance with claim 15, wherein said membrane is composed of a vapor permeable and liquid impermeable material.

19. A trapping device for frugivorous insects, the device comprising:
an insect retaining structure comprising an upper portion and a bottom portion, said upper portion being connected to said bottom portion, said insect retaining structure comprising at least one opening, said upper portion having an upper portion inner surface, said bottom portion having a bottom portion inner surface, said upper portion inner surface and said bottom portion inner surface defining an insect retaining structure chamber, said insect retaining structure chamber being in communication with said at least one opening; and
a single diffuser arranged in said insect retaining structure chamber, said single diffuser comprising an attractant solution retaining structure, said attractant solution retaining structure being composed of a liquid and vapor impermeable material, said attractant solution retaining structure having an interior space, said attractant solution retaining structure comprising a support material arranged in said interior space, said support material comprising a *Ceratitis Capitata* insect attractant solution comprising 1,5-diaminopentane, ammonium acetate and trimethylamine, said *Ceratitis Capitata* insect attractant solution being in a liquid state, said attractant solution retaining structure comprising a liquid barrier composed of a vapor permeable and liquid impermeable material, wherein vapor from said *Ceratitis Capitata* insect attractant solution diffused into said insect retaining structure chamber via said liquid barrier.

* * * * *